United States Patent [19]

Jung et al.

[11] Patent Number: 5,021,350
[45] Date of Patent: Jun. 4, 1991

[54] PROCESS FOR INCLUSION OF MYCORRHIZAE AND ACTINORHIZAE IN A MATRIX

[75] Inventors: Gerard Jung, Montlhery; Jacques Mugnier, Chasieu; Yvon Dommergues, Saint Mande; Hoang G. Diem, Billy Montigny, all of France

[73] Assignee: Rhone-Poulenc Industries, Cour Bevoie, France

[21] Appl. No.: 364,554

[22] Filed: Jun. 8, 1989

Related U.S. Application Data

[63] Continuation of Ser. No. 37,127, Apr. 9, 1987, abandoned, which is a continuation of Ser. No. 921,891, Oct. 21, 1986, abandoned, which is a continuation of Ser. No. 352,946, Feb. 26, 1982, abandoned.

[30] Foreign Application Priority Data

Mar. 6, 1981 [FR] France ................... 81 04474

[51] Int. Cl.$^5$ ............ C12N 1/00; C12N 11/10; C12N 11/08; C12N 11/04; C12N 1/12; C12N 1/14
[52] U.S. Cl. .................. 435/243; 435/178; 435/180; 435/182; 435/252.1; 435/254
[58] Field of Search ..... 435/243, 260, 189, 252.1–256, 435/178, 179, 181, 910, 830, 182, 911; 71/6, 7, 902, 904

[56] References Cited

U.S. PATENT DOCUMENTS

| 1,909,622 | 5/1933 | Matchette . | |
|---|---|---|---|
| 2,901,864 | 9/1959 | Hiler | 47/58 |
| 2,988,455 | 6/1961 | Rosenberg et al. | 106/169 |
| 2,995,867 | 8/1961 | Burton | 47/1 |
| 3,034,968 | 5/1962 | Johnston | 195/98 |
| 3,168,796 | 2/1965 | Scott et al. | 47/1 |
| 3,472,644 | 10/1969 | Woodside et al. | 71/1 |
| 3,765,918 | 10/1973 | Jordan et al. | 106/205 |
| 3,822,187 | 7/1974 | du Chaffaut et al. | 195/28 R |
| 3,898,132 | 8/1975 | Hettrick | 195/65 |
| 4,038,140 | 7/1977 | Jaworek et al. | 195/63 |
| 4,089,746 | 5/1978 | Masri et al. | 195/63 |
| 4,119,429 | 10/1978 | Lovness | 71/6 |
| 4,146,706 | 3/1979 | Hisatsuka et al. | 536/1 |
| 4,155,737 | 5/1979 | Dommergues et al. | 71/7 |
| 4,202,905 | 5/1980 | Asai et al. | 426/1 |
| 4,211,774 | 7/1980 | Kang et al. | 424/181 |
| 4,352,883 | 10/1982 | Lim | 435/178 |
| 4,376,113 | 3/1983 | Suglia et al. | 424/34 |
| 4,434,231 | 2/1984 | Jung | 435/253 |

FOREIGN PATENT DOCUMENTS

| 977178 | 11/1975 | Canada . | |
| 1029839 | 5/1958 | Fed. Rep. of Germany . | |
| 7308830 | 3/1973 | Japan . | |
| 0628143 | 12/1978 | U.S.S.R. | 71/6 |
| 1177077 | 1/1970 | United Kingdom . | |
| 1267685 | 3/1972 | United Kingdom . | |
| 1526317 | 9/1978 | United Kingdom . | |
| 1556584 | 11/1979 | United Kingdom . | |

OTHER PUBLICATIONS

Jung: Chem. Abstr. 93:237798 (1980).
M. E. Fraser, "A Method of Culturing *Rhizobium meliloti* on Porous Granules to Form a Pre-Inoculant for Lucerne Seed," 39 *J. Appl. Bact.* 345-351 (1975).
G. A. Hunt et al., "Preservation of Cultures by Drying on Porcelain Beads," 76 *J. Bacteriology* 453-454 (1958).
F. Munevar et al., "Growth of *Rhizobium japonicum* Strains at Temperatures Above 27¼C," 42 *Applied and Environmental Microbiology* 272-276 (1981).
V. Patrikeyev et al, "Method of Producing Dry Microorganisms," 4 *Microbiology Abstracts: A Industrial Microbiology* A4153 (1969).
J. Pena-Cabriales et al., "Survival of Rhizobium in Soils Undergoing Drying," 43 *Soil Sci. Soc. Am. J.* 962-966 (1979).
M. Salema et al., "Death of Rhizobia on Inoculated Seed," 14 *Soil Biol. Biochem.* 13-14 (1982).
Vincent, "Rhizobium", 25 *Newsletter* 136 (1981).
J. H. Graham et al., "Ethylene Production by Ectomycorrhizal Fungi, *Fusarium oxysporum* f. sp. pini, and by Aseptically Synthesized Ectomycorrhizae and Fusarium-Infected Douglas-Fir Roots," 26 *Can. J. Microbiol.* 1340-1347 (1980).
M. Lalonde et al., "Production of Frankia Hyphae and Spores as an Infective Inoculant for Alnus Species," *Symbiotic Nitrogen Fixation in the Management of Temperate Forests* 95-110 (proceedings of a workshop held at Oregon State University on Apr. 2-5, 1979).
M. Lalonde, "Confirmation of the Infectivity of a Free-Living Actinomycete Isolated from *Comptonia peregrina* Root Nodules by Immunological and Ultrastructural Studies," 56 *Can. J. Bot.* 2621-2635 (1978).

(List continued on next page.)

*Primary Examiner*—James Martinell
*Attorney, Agent, or Firm*—Richard M. Barnes; Theresa L. Solomon; Michael P. Morris

[57] ABSTRACT

This invention relates to a process of inclusion of microorganisms of the group consisting of mycorrhizae and actinorhizae in a polymer gel matrix to prepare a solid, stable, storable preparation suitable for use in particular for agronomic purposes. The polymer gel matrix is based on at least one polymer from the polysaccharide group, with at least partial cross-linking of the polymer.

13 Claims, No Drawings

OTHER PUBLICATIONS

D. Marx, "The Influence of Ectotrophic Mycorrhizal Fungi on the Resistance of Pine Roots to Pathogenic Infections II. Production, Identification, and Biological Activity of Antibiotics Produced by *Leucopaxillus cerealis* var. piceina," 59 *Phytopathology* 411–417 (1969).

A. Quispel, "Symbiotic Nitrogen Fixation in Non-Leguminous Plants," 9 *Acta Botanica Neerlandica* 380–396 (1960).

I. Takata et al., "Screening of Matrix Suitable for Immobilization of Microbial Cells," 2(3) *J. Solid-Phase Biochem.* 225–36 (1977).

J. Janzen et al., "Specific Surface Area Measurements on Carbon Black," 44 *Rubber Chem. and Tech.* 1287–1296 (1971).

S. Brunauer et al., "Adsorption of Gases in Multi-Molecular Layers," 60 *J. Am. Chem. Soc'y* 309–319 (1938).

G. Bond, "Some Reflections on Alnus-Type Root Nodules," *Recent Developments in Nitrogen Fixation* (Newton, Postgate and Rodriguez-Barrueco eds., Academic Press 1977), pp. 531–537.

M. Lalonde et al., "Formation de Nodules Racinaires Axeni ques chez *Alnus crispa* var. mollis," 50 *Can. J. Bot.* 2597–2600 (1972).

N. Amarger et al., "Influence of the Age of the Culture on the Survival of *Rhizobium meliloti* After Freeze Drying and Storage," 81 *Arch. Mikrobiol.* 361–366 (1972).

PROCESS FOR INCLUSION OF MYCORRHIZAE AND ACTINORHIZAE IN A MATRIX

This application is a continuation of U.S. application Ser. No. 037,127, filed Apr. 9, 1987, entitled 'Process For Inclusion of Myccorrhizae and Actinorhizae in a Matrix,' now abandoned, which in turn was a continuation of U.S. application Ser. No. 921,891, filed Oct. 21, 1986, now abandoned, which in turn was a continuation of U.S. application Ser. No. 352,946, filed Feb. 26, 1982, now abandoned.

BACKGROUND OF THE INVENTION

The invention concerns a method of inclusion of microorganisms of the group consisting of mycorrhizae and actinorhizae in a matrix comprising a polymer gel, to prepare a product suitable for use in particular for agronomic purposes.

It was proposed many years ago to fix microorganisms on a carrier in U.S. Pat. No. 1,909,622, in which nitrogenfixing bacteria of the genus Rhizobium are used.

Generally, however, the microorganism culture is adsorbed onto a carrier, as in Belgian patent 521,850, which advocates the use of diatomaceous earth and colloidal silica for Rhizobium. Bentonite has also been used (in British Patent No. 1,777,077), as have plaster granules (in French Patent No. 1,490,046) and even lignite.

This method of inclusion by adsorption has disadvantages, particularly in connection with the survival of the microorganism and its protection during transport, storage and handling. Since this procedure gives only very limited results, attempts have been made to improve fixing techniques.

Thus, French Patent No. 1,180,000 calls for the use of a must juice, to which substances with an adsorbing action are added, such as cellulose, bone meal, kaolin or silica gel, in the manufacture of preparations rich in bacteria of the Azotobacter group. This type of preparation is also not satisfactory.

Attempts have therefore been made to improve both the survival rate of the microorganisms, e.g., by inclusion, and the manner of bringing them into the plant medium. Thus, in French Patent application No. 77.10254 of Apr. 5, 1977 (corresponding to U.S. Pat. No. 4,155,737) a method is proposed which makes use of an inoculum comprising a polymer gel with microorganism included therein. The inoculum is introduced into the rhizosphere of the plants. According to this patent, the polymer gel may be a polyacrylamide gel or a silica gel.

None of the above methods has been entirely satisfactory in meeting all of the requirements for an adequate carrier. Such a carrier must maintain the microorganism under conditions sufficient to preserve, protect and keep it in a suitable form for handling, while at the same time enabling it to swarm into the medium and if possible allowing for the grafting of additives onto the carrier. Furthermore, the carrier must insure the viability of the microorganism, even after periods of several weeks and under conditions of variable hygrometry. This means that the carrier must be able either to contain a sufficient reserve of water, which can be made available as necessary, or to obtain the necessary water from the environment. Finally, the carrier must not be detrimental to the environment, i.e., it must be either biodegradable or non-polluting.

This rapid enumeration of requirements, which makes no claim to be exhaustive, suggests why until now a suitable method has not been developed as expected.

In French Patent application 79.08597 of Apr. 5, 1979, there is disclosed a particularly attractive method, comprising the inclusion of the microorganism in a polymer of the polysaccharide group and an at least partial cross-linking of the polymer, e.g., by heat treatment, through use of a metal salt or through synergism with another polymer. This method gives surprising results, and a remarkable synergism is shown when a compound which is absorbent and adsorbent, such as a silica, is also used.

The above-noted French patent application is directed in particular to preparations of *Rhizobium japonicum*, a non-sporulated, nitrogen fixing bacterium which is very sensitive to drying, temperature and physico-chemical factors. Some microorganisms, however, present additional difficulties because of their fibrous nature, such as ectomycorrhizian fungi (e.g., Pisolithus, Hebeloma, Tuber, Boletus, etc.) which, moreover, have no form of resistance to, e.g., pathogenic germs, when cultivated in pure culture.

Mycorrhizian associations are the result of associating a fungus with a root, leading to a true symbiosis. The following groups are distinguished by the nature the association:

(a) ectotrophic mycorrhizae, found chiefly in woodland trees (Pinaceae, Fagaceae), most being upper fungi (Ascomycetes and Basidiomycetes); and (b) endotrophic mycorrhizae, usually lower fungi (Phycomycetes), much more common than the above and found in trees, shrubs and herbaceous plants in the case of mycorrhizae with arbuscles and vesicles, but limited to Ericaceae in the case of mycorrhizae with clusters.

The beneficial action of these mycorrhizae on the growth of plants can be attributed to plant hygiene protection against pathogens in the ground, production of growth-promoting substances or vitamins improvement in the mineral nutrition of the plant (particularly with respect to phosphorous) through an increase in the possibilities for ground exploration, and improvement in water absorption where there is a shortage of water.

In the case of nitrogen-fixing non-leguminous plants, symbiotic associations of the same type as those existing between Rhizobium and leguminous plants are characterized by the formation of nodules on the root system. These are found both in trees and shrubs and in herbaceous plants. The function of the nodules is known only in certain ligneous plants which generally colonize poor or degraded soils (sands, moraines), where real fixation of atmospheric nitrogen has been shown to take place. 137 species of Angiospermae belonging to 12 different genera, classed in seven families (Betulaceae, Casuarinaceae, Coriariaceae, Eleagnaceae, Myricaceae, Rhamnaceae, Rosaceae) have been recognized (Bond 1974). The endophyte responsible for forming the nitrogen-fixing nodules is an Actinomycetum (Frankia) which had only been isolated in pure culture in 1978 by Lalonde et al. (Laval University, Quebec).

There is no doubt of the importance of using these nitrogen-fixing varieties of microorganisms in sylviculture, particularly in marginal soils which are poor in nitrogen and with a modified structure or none at all. The following examples can be given as an indication of typical uses:

(1) reforestation of peat bog in France (Aulne, Myrica), glacial moraines in the Alps (Aulne), soil thrown up in mining or quarrying oil shale in the U.S.A.;

(2) fixing maritime and continental dunes in Senegal (Casuarina);

(3) developing James Bay in Canada;

(4) *Alnus rubra* - Douglas associations in the N.W. American forest systems;

(5) use of *Alnus glutinosa, A. cordata, A. incana, A. crispa* as nurse trees to encourage development of non-fixing species;

(6) use of Ceanothus, Myrica, Hipophaca, Eleagnus in association with non-fixing species or in production of green fertilizer or biomass.

Inoculation has been traditionally carried out at the nursery stage, using crushed nodules. This has the serious disadvantages that pathogenic germs may be introduced into the inoculum and that the nodules cannot be preserved, even at low temperature, because of the rapid oxidation of tannins and phenolic substances, which are toxic to the microorganisms. It has not thus far been possible to demonstrate in a formal manner that the productivity of these species can be increased by inoculating with an endophyte developed in pure culture.

With ectomycorrhizae, inoculation has traditionally been carried out using soil from another nursery; currently, it is more common to use pure cultures of mycorrhizian fungi in vermiculite. Inoculation carried out in this way has three major disadvantages:

(1) the difficulty in developing the fungus (e.g., Pisolithus or Hebeloma): At least six weeks time is required (Grahan-Linderman 1980 Can. J. Microb. 26, II) to obtain a thin, heterogeneous culture in a liquid medium; at least eight to ten weeks is required on vermiculite. In the case of a liquid culture, it is necessary to recover the mycelium and crush it before use, with the dangers of excessive shearing leading to no regrowth. This is particularly true for Tuber, since the microorganism has only hyphae and no form of resistance.

(2) the large quantity of inoculum required: 2 l/m² in the case of microorganisms developed on vermiculite, with the corresponding difficulty in storage; and (3) the need to inoculate with inocula which have been freshly prepared or stored at 4° C. It is these problems which have led to the development of the instant invention.

One object of the invention is to develop an inoculum which can be stored at ambient temperature and is easy to use.

Another object is to improve the properties of cultures of mycorrhizae and actinorhizae, particularly with respect to the level of homogeneity.

Still another object of the invention is to achieve a reduction of cultivation time, in particular for actomycorrhigae

GENERAL DESCRIPTION OF THE INVENTION

The present invention is concerned with a process of inclusion of a microorganism from the group consisting of mycorrhizae and actinorhizae in a matrix comprising a polymer gel based on at least one polymer from the polysaccharide group, with at least partial cross-linking treatment of the polymer.

In accordance with the invention the "at least partial cross-linking treatment" is understood as being a treatment which can modify the structure of the polysaccharide, such as heat treatment, treatment with a metal salt or a synergistic treatment using a different polymer and preferably a different polysaccharide.

The polymer is advantageously based on a heteropolysaccharide of high molecular weight, obtained by fermenting a carbohydrate with a microorganism of the genus Xanthomonas or Arthobacter or with fungi of the genus Sclerotium.

Polymers obtained from natural or biosynthetic gums from various sources may also be used, for example: algae (alginates, carrageenans, agar), exudates of plants (gums such as karaya, tragacanth, arabic) or seeds (guar, carob).

Locust bean gum is an extract from the fruit of the carob tree (*Ceratonia siliqua L.*), a tree of the family Caesalpiniaceae (geographical area: Mediterranean basin). Locust bean gum is contained in the endosperm of the seed. The endosperm is separated from the embryo by mechanical abrasion or a chemical process. Locust bean gum is a polysaccharide (galactomannan) consisting of $\beta$-D-mannopyranosyl units (bonds 1–4), one out of four or five being substituted at $C_6$ by $\alpha$-D-galactopyranosyl.

The combination of xanthan gum with locust bean gum by a synergistic effect increases the viscosity of the gel. It is believed that the xanthan gum is made up of helical chains and that interaction with galactomannan leads to the formation of bonds between the chains, enabling a gel with a three-dimensional network to be obtained.

The alginates are refined extracts of brown algae of the Phaeophyceae class. Alginic acid is a straight polymer of high molecular weight formed by a succession of molecules of $\beta$-D-mannopyranosyluronic acid and $\alpha$-L-gulopyranosyluronic acid. The addition of calcium ions links two carboxyl groups, forming a bridge between parallel chains, particularly in the regions consisting of guluronic acid. In this manner, a gel of higher viscosity is obtained instantly at 25° C. Conversely, the addition of phosphate ions enables solidification to be retarded; this may be helpful for handling the preparation before it is completely gelled.

As indicated in French Patent application 79.08597 (European Patent application 17 565), the concentration of microorganisms in the preparation may be increased by filtering or centrifuging the culture medium, resuspending the filtrate or bottom in a small volume and adding it to the polysaccharide solution.

The microorganism or microorganisms may be added in various ways. Generally, a culture medium is first prepared, which is seeded with the microorganism; the culture medium, or the suspension of the microorganism obtained by filtering and centrifuging, is then added to the polysaccharide solution; and a gel is finally formed by cooling.

In particular, in a first embodiment of the invention, a polysaccharide solution is first formed hot and brought to a temperature of approximately 40° to 45° C. The culture medium containing the microorganism, or the suspension of the microorganism, is then added and the mixture is cooled to form the gel.

In another embodiment, the culture medium or microbial suspension is added separately to each polysaccharide solution under the same temperature conditions. The substances are then mixed and cooled to form the gel.

As noted above, it is also possible to use a metal salt such as one of iron or aluminum, which may or may not be complexed with a polyol.

Alternatively, the polysaccharide may be dissolved in the culture medium, particularly at ambient temperature, and the cross-linking carried out in situ.

As previously mentioned, the microorganism of the invention may be an actinorhiza such as the endophytic actinomycetum of a non-leguminous plant, or a mycorrhiza, ectomycorrhiza or endomycorrhiza.

The inocula may be in various forms: gel, powder, pellets or even fibers. The actinomycetum may be provided in the form of liquid culture or in the form of crushed nodules.

It is advantageous to dry the gel. As already mentioned, the microorganism is known to be generally very sensitive to heat. Ordinary drying takes a long time and gives a dry film which crumbles easily and can be crushed without difficulty. It is therefore preferable to add an absorbent substance with a large capacity for absorbing water to the gel, so that the residual water content obtained in the gel plus absorbent mixture is from 70 to 250 g/100 g of absorbent and advantageously from 100 to 150 g/100 g.

The absorbent substance is a porous material such as natural or synthetic silica, silico-aluminates, cellulose, etc. The pH is in the region of 7, and the drying temperatures are low enough not to destroy the microorganism, e.g., on the order of 20° to 30° C.

The material may be put into its final form in various ways.

In a first embodiment, the gel is dried and then finely crushed, a substance such as silica is added to it and the two are homogenized. The resultant powder can then be put into tablet form.

In another embodiment, the moist gel and the substance such as silica are placed in a mixer. After being worked, the mixture may be spread out and dried directly, until the loss of water is from 0 to 50% of its weight but preferably from 30 to 40%, giving a powder with a residual water content of from 100 to 150 g per 100 g of absorbent material. Alternatively, the mixture is placed in an extruder and the granules obtained are dried at ambient temperature, again until there is a loss of water of from 30 to 40%.

In cases where the microorganism is a mycorrhiza, this may advantageously be put into the form of a homogeneous mycelian culture. The inoculum may be in the form of moist pellets, threads or fibers.

In a first embodiment, the volume of liquid culture may be converted to a substantially identical volume of solid, so that moist pellets can advantageously be obtained. In a second embodiment, the gel obtained when the culture or suspension of the microorganism has been included has an absorbent substance added to it, so as to give a powder which can easily be handled. The absorbent substance is advantageously a silica, its percentage by weight relative to the gel being from 10 to 120% and preferably 30 to 50%.

In both embodiments, the process has the considerable advantage that the mycelium does not have to undergo any mechanical treatment such as shearing or crushing. In addition, the process provides inocula which can be stored at ambient temperature, under non-sterile, non-contaminating conditions.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims.

EXAMPLE 1: Endophytic actinomycetum of non-leguminous plant

1. Stock - Isolation - Cultivation - Preservation

Symbiosis studied: *Alnus glutinosa* - Frankia

Stocks: Frankia ARbNN4b and AgNlag (Lalonde Collection, Faculty of Forestry and Geodesy, Laval University, Quebec).

Isolation of Frankia from nodule (technique developed by Lalonde et al. Proc. Workshop 2.5/4-1979-Corvallis-Oregon).

An end of a coralloid nodule is surface-sterilized (30% $H_2O_2$ for 5 minutes; then 5% NaClO for 30 minutes). It is rinsed with sterile water. The nodule is placed in a salt cellar containing a 1% solution, which is sterilized by filtering polyvinylpyrrolidone (PVP)+phosphate buffer (PBS (g/l)=NaCl, 0.8; $Na_2HPO_4 \cdot 7H_2O$, 1.14; $KH_2PO_4$, 0.2). The lower part of the nodule is sectioned and the end transferred to a different salt cellar containing PBS (a few drops). The nodule is crushed and the inside is taken out and used to seed a test tube containing Q mod* medium (Quispel 1960, as modified by Lalonde 1979).

*Q mod (g/l): $K_2HPO_4$, 0.3; $NaH_2PO_4$, 0.2; $MgSO_4 \cdot 7H_2O$, 0.2; KCl, 0.2; Yeast Extract (BBL), 0.5; Bactopeptone (DIFCO), 5; glucose, 10; ferric citrate (citric acid+ferric citrate solution 1%), 1 ml; oligo-elements, 1 ml; $H_2O$ to give 1000 ml (pH 6.8–7.0); $CaCO_3$, 0.1; lecithin, 5 mg. Sterilization: 20 minutes at 120° C. The material is incubated for two weeks at 27° C.

CULTIVATION

After incubation, the mycelium is split up with a syringe and 6 tubes are reinoculated. The same procedure is carried out every two weeks, as a means of actively multiplying the Actinomycetum. Before each planting out process the culture is washed with PBS. The colony is taken from the bottom of the tube with a pipette and transferred to a Q Mod medium.

PRESERVATION - GERMINATION OF SPORES

Germination of spores in a culture which has been stored for several months is encouraged by immersing the colony in a solution consisting of 45 mg alanine+60 mg leucine+50 ml PBS for 30 minutes and by returning it to the Q mod medium after splitting it up.

2. CULTIVATION OF PLANTS (*ALNUS GLUTINOSA*)

A. Pregermination of seeds

This operation includes four phases:

(1) SELECTION OF SEEDS

The seeds are placed in a beaker containing hexane (d=0.66). Those which drop to the bottom are taken out and dried on paper, and the floating seeds are discarded.

(2) DORMANCY SPROUTING

The seeds are placed in water and put at +4° C. for 4 days.

(3) STERILIZATION

This is carried out in 5% NaClO for 5 minutes, followed by washing with sterilized distilled water.

(4) PREGERMINATION

The seeds are placed on a medium which has been treated with gelose, on a Petri dish, containing 1% of gelose and 1.5% of saccharose. The Petri dishes are arranged upside down in a chamber saturated with water, and are kept at 28° C. in the dark for 6 days.

B. Pricking out plantlets

The non-contaminated plantlets are pricked out into "Pouches" or test tubes with a diameter of 22 mm.

(1) Pricking out into "Pouches"

Filter paper with a spout at the top is placed in a polyethylene bag (10×20 cm). 8 ml of Crone solution (as modified by Lalonde, J. Can. Botanic 50, 2597-2600 (1972)), without any nitrogen, diluted by ½ in the bag, is poured in so as to moisten the whole filter. Holes are made in the spout, and the plantlets are arranged with their rootlets facing the opening and so that the cotyledons extend beyond the spout. The bags are placed in a controlled room (lighting 15000 lux, photoperiod 14 hours, temperature from 19° to 23° C.).

(2) Planting out onto vermiculite

Tubes with a diameter of 22 mm are filled with 40 ml of vermiculite washed with water. 20 ml of Crone solution, diluted by ½, is added, after which the whole arrangement is sterilized for 20 minutes at 120° C. The plantlets are pricked out and incubated as above.

3. PREPARATION OF INOCULA

3.1 INOCULA WITH INCLUDED FRANKIA CULTURE

Frankia colonies obtained from 10 cultures in test tubes, which have developed for 15 days, are taken out, resuspended in 55 ml of PBS and split up. The inocula are prepared with this concentrated suspension, containing hyphae, spores and spore cases, as follows:

INOCULUM BASED ON ALGINATE (AlG)

The concentrations are given for the preparation of 45 g of gel. 0.45 g of alginate is dissolved in 36 ml of suspension; 9 ml of a 6 g/l solution of $CaSO_4 \cdot 2H_2O$ is stirred in. The gel obtained is then either dried in air until dehydrated, or 40% of its weight of silica is added and the two are mixed until a moist homogeneous powder is obtained. The powder is then dried at ambient temperature until the inoculum contains only 125 g of water per 100 g of silica.

INOCULUM BASED ON XANTHAN GUM + LOCUST BEAN GUM (XG)

The concentrations are given for preparing 45 g of gel. 225 mg of xanthan gum is dissolved in 15 ml of distilled water at approximately 70° C. The same procedure is followed with 225 mg of locust bean gum instead of the xanthan gum. When the two solutions are at about 45° C., 7.5 ml of suspension is stirred into each. The mixture of suspension + carob seeds is then poured into the mixture of suspension + xanthan gum. The preparation is cooled to give a gel. The gel is either dried in air until dehydrated, or as with the AlG gel, 40% of its weight in silica is added to it. The mixture is dried at ambient temperature until the content of residual water is 125 g per 100 g of silica.

3.2 INOCULA WITH CRUSHED NODULE INCLUSIONS 100 ml of freshly picked *Alnus glutinosa* nodules are washed and then ground in a mixer, to give approximately 300 ml of a homogeneous suspension, which will be used to prepare gels based on alginate or xanthan gum with crushed nodule inclusions. The gels are air dried, then reduced to powder form.

INOCULA BASED ON ALGINATE (AlG)

For the preparation of 200 g of gel: 2 g of alginate is dissolved in 160 ml of suspension. 40 ml of a 6 g/l solution of $CaSO_4 \cdot 2H_2O$ is added to form a gel. Part of the gel is dried to total dehydration at ambient temperature; another part has 40% of its own weight of silica added to it, and is then dried until the content of residual water is 125 g per 100 g of silica.

INOCULA BASED ON XANTHAN GUM - LOCUST BEAN GUM

For the preparation of 360 g of gel: 1.8 g of xanthan gum is dissolved in 120 ml of water at 70° C., for 20 minutes with agitation, then the temperature is returned to about 45° C. The same procedure is carried out with 1.8 g of locust bean gum instead of the xanthan gum. When the two solutions are at about 45° C., 60 ml of the suspension of crushed nodules is added to each. The preparation is cooled to give a gel. Part of this is dehydrated, and the other part has silica added to it as with the alginate gel.

4. RESULTS

4a. TEST IN "POUCHES"

The survival of the microorganism after inclusion, drying and storage at ambient temperature (20°-25° C.) has been checked on plantlets of *Alnus glutinosa* by the "Pouches" method described above. The plantlets arranged in the bag are developed for 10 days under controlled conditions, then they are inoculated by depositing the inoculum to be studied below the end of the main root. If inoculation is effective and the microorganism live, swellings will appear 10 to 20 days after inoculation, then small nodules on the root at the place where the inoculum was deposited. The results obtained with inocula based on AlG or XG gel + silica which have been stored for 10 to 20 days at ambient temperature are set out in Table I below.

TABLE I

Influence of type of inoculum on nodulation of *Alnus glutinosa*

| Inoculum | Preservation (days) (4) | Quantity of inoculum per plant | No. of nodulated plants/total no. of plants |
| --- | --- | --- | --- |
| Not inoculated | — | 0 | 0/18 |
| Suspension of crushed nodules[1] | 0 | 0.25 ml | 5/6 |
| Crushed nodules included in dry XG[2] | 20 | about 5 mg | 4/4 |
| ARbNN4b Liquid culture[3] | 0 | 0.25 ml | 1/5 |
| included in XG + silica[5] | 70 | 5 mg | 6/9 |
| included in AlG + | 70 | 5 mg | 6/9 |

TABLE I-continued

| | Influence of type of inoculum on nodulation of *Alnus glutinosa* | | |
|---|---|---|---|
| Inoculum | Preservation (days) (4) | Quantity of inoculum per plant | No. of nodulated plants/total no. of plants |
| silica AgNlag liquid culture[3] | 0 | 0.25 ml | 6/6 |
| included in XG + silica[5] | 20 | 5 mg | 5/6 |

[1] 150 mg fresh nodules/5 ml $H_2O$
[2] drying in air H = 12%
[3] culture used as inclusion
[4] preservation of inoculum at ambient temperature (20 to 25° C.)
[5] precipitated silica — BET surface area = 200 m$^2$/g — CTAB = 80 m$^2$/g. BET surface: determined in accordance with the Brunauer-Emmett-Teller method, described in Journal of the American Chemical Society 60, p. 309 (1938). CTAB surface: outer surface by absorption of cetyl trimethyl ammonium bromide at pH 9, in accordance with the method described by Jay, Janzen and G. Kraus in Rubber Chemistry and Technology 44, p. 1287-1296 (1971).

It will be seen that there is approximately 100% nodulation in the cases where the inocula are prepared from included microorganisms+silica, although the quantity of culture used in 5 mg is 50 to 100 times less than that used in 0.25 ml of liquid inoculum.

4. TESTS ON VERMICULITE

The infectivity and effectiveness of the microorganism (stock ArbNN4b) after inclusion and storage at ambient temperature (20° to 25° C.) have been tested with *Alnus glutinosa* developed in test tubes containing vermiculite+nutrient medium without any nitrogen (Crone solution). The results obtained are given in Table II.

TABLE II

| | Influence of type of inoculum on nodulation and growth of *Alnus glutinosa* (age of plantlets 50 days) | | | | |
|---|---|---|---|---|---|
| Inoculum | Preservation (days) (2) | No. Nodules/ 6 Plants | Weight in mg of green aerial part/ 6 Plants | Average height of Plants mm | Appearance of Plants |
| Not inoculated | — | 0 | 182 | 31 | chlorosis |
| | | 0 | 195 | 42 | chlorosis |
| liquid culture | 0 | 9 | 331 | 50 | green |
| Included in XG + silica[1] | 15 | 30 | 468 | 56 | green |
| Included in XG + silica[1] | 30 | 36 | 515 | 59 | green |
| Included in AlG + silica | 30 | 32 | 444 | 62 | green |

[1] Culture used as inclusion.
[2] Preservation of inoculum at ambient temperature (20-25° C.)

These results show a certain novelty in this field, since this is the first time that anyone has succeeded in preparing inocula which included endophyte (pure culture of Frankia or suspension of crushed nodules), with the following advantages:

(1) inocula in powder form, easy to handle;
(2) possible use in very small volumes;
(3) microorganisms included retain their infectivity when stored at ambient temperature; and
(4) no problem of contamination by external agents.

The process of including crushed nodules of Casuarina in an air-dried alginate gel has been used, in particular, for inoculating 600,000 Casuarina stock in Senegal, as part of a project for immobilizing maritime and continental dunes.

EXAMPLE 2: Mycorrhizae

1.1: STOCK USED

*Pisolithus tinctorius* (Marx)

1.2: CULTIVATION OF MICROORGANISM IN LIQUID MEDIUM

As a general rule the fungus is maintained and cultivated on a Marx medium as modified by Melin-Norkrans (MMN)*. Under these conditions fermentation takes from 6 to 8 weeks.

*MMN (g/l): $CaCl_2$, 0.05; NaCl, 0.025; $K_2HPO_4$, 0.5; $(NH_4)_2HPO_4$, 0.25; $MgSO_4 \cdot 7H_2O$, 0.15; Ferric Citrate, 1 ml (1% Fe citrate); thiamine, 100 μm; malt extract, 3.0; saccharose, 10.0; $H_2O$ to make 1000 ml (pH=5.5).

One of the cultivating sequences adopted for Pisolithus is given below:

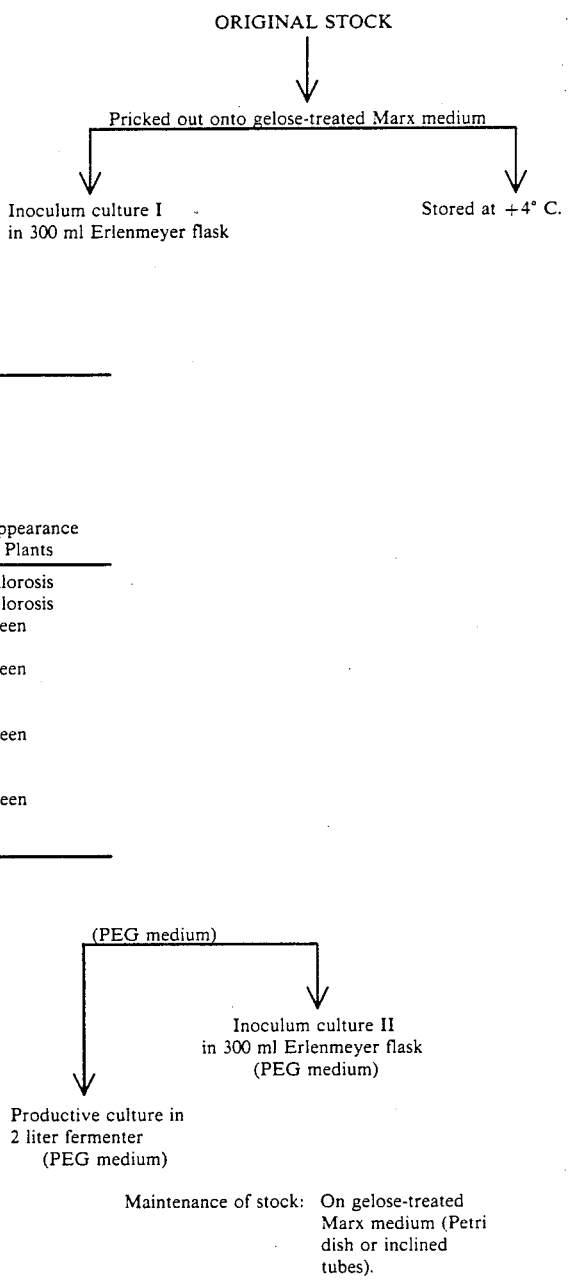

INOCULUM CULTURE I receptacle: 300 ml Erlenmeyer flask plugged with polyurethane cotton, filled with 70 ml of culture medium.

PEG culture medium (g/l): peptone, 10; yeast extract, 5; glucose, 10; gelose, 1; pH=approximately 7; sterilization; 25 minutes at 120° C.; pH after sterilization=approximately 6.6;

seeded from a culture on gelose (fragments of gelose+mycelium);

conditions: incubated 10 to 15 days on agitating table rotating at 100-140 rpm, tray 25 mm off center, temperature 28° C.

INOCULUM CULTURE II

The cultivating conditions are the same as above, but seeding takes place from culture I in quantities of 5 to 10%, and the incubating time is reduced to one week.

| Productive culture in 2 liter fermenter (Biolafitte) | |
|---|---|
| filling: | 1000 ml |
| medium: | PEG described above |
| seeding: | 1 to 10% |
| conditions: | agitation with turbine turning at 250-300 rpm, aeration 20 l/hour, temperature 25 to 30° C. |

RESULTS

After 8 to 13 days of cultivation in a 2 liter fermenter, a dense, homogeneous culture is obtained, thereby avoiding any subsequent crushing of the mycelium before the inoculum is prepared. The quantity of biomass (dry weight at 105° C.) obtained per liter of medium is in the vicinity of 2.5 g/l.

1.3 PREPARATION OF INOCULA WITH INCLUDED MICROORGANISMS

Since ectomycorrhizian fungi do not have any form of resistance when cultivated in pure culture, it is necessary to retain a certain content of residual water when the inoculum is being prepared, in order to insure the survival of the mycelium. This type of inoculum has been made either by adding silicas to the gel following the inclusion of the fungus in a gel based on polysaccharides, or by mixing the mycelium suspension with alginate and letting the mixture fall drop by drop into a concentrated solution of $CaCl_2$, on the principle described by Hackel in 1977 as applied to the immobilization of Rhizobium (French patent application 79.28956 (1979)).

INOCULUM IN POWDER FORM

The culture developed in a 2 liter fermenter is filtered or centrifuged, washed and suspended in physiological salt solution. The suspension is used to prepare gels based on alginate or xanthan gum, by the methods described previously for Frankia.

The gels then have synthetic or natural silica added to them and are mixed, then dried, until the residual water content is from 70 to 250%, thus giving moist or partially dehydrated powders which are kept in sealed bottles.

INOCULUM IN FORM OF ALGINATE PELLETS

From 1 to 2 g/l of alginate is dissolved in the mycelium suspension, then the mixture is added drop by drop to a concentrated 170 g/l solution of $CaCl_2$. The pellets formed are rapidly removed, then washed in tap water and kept in sealed bottles.

The effective life of the fungus (*Pisolithus tinctorius*) in the preparation, particularly in the case of alginate pellets, is over six months at ambient temperature. The test used to assess survival is based on the principle of colorimetric determination of respirometric activity by reducing Nitro Blue Tetrazolium to formazan, a compound colored blue. The infectivity and effectiveness of the inocula is tested on *Pinus caribaea* or *Pinus pinaster* when the pellets have been redissolved by means of a decomplexing agent, such as phosphates, citrate, lactate, etc.

These tests illustrate the progress made in the preparation of inocula with actomycorrhizae. The cultivating of currently used mycorrhizian fungi in a liquid medium is improved with respect to production of homogeneous biomass and reduction of fermentation time by four to six weeks. Moreover, the procedure allows for the preparation of inocula which are easy to use and enable the microorganism to survive for several months.

The method of preparing inocula with Frankia and ectomycorrhizae may also, for example, be applied to the inclusion of endomycorrhizae with clusters developed in pure culture, and to the inclusion of crushed roots mycorrhiza (treated by endomycorrhizae with vesicles and arbuscles). Inocula prepared by including roots which have been infected then crushed (mycelium+spores) in XG or AlG gels with silica added retain their infectivity: the endomycorrhizian fungus with vesicles and arbuscles is present on the roots of the test plant inoculated by this process.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

We claim:

1. A method of preparing and storing a stable, storable homogeneous preparation of a mycorrhizae microorganism, said method comprising embedding said mycorrhizae microorganism in the form of a liquid mycelian culture in a polymer gel matrix based on at least one polymer from the polysaccharide group, the volume of the resulting polymer gel matrix being substantially the same as the volume of said liquid culture, and storing the resulting homogeneous preparation of a mycorrhizae microorganism in the polymer gel matrix in the form of a homogeneous moist preparation.

2. The method of claim 1, wherein the polymer is cross-linked by heat treatment.

3. The method of claim 1, wherein cross-linking is effected by the action of a metal salt.

4. The method of claim 3, wherein the polysaccharide is dissolved in the culture medium or suspension of the microorganism at ambient temperature, and the cross-linking is formed in situ.

5. The method of claim 1, wherein cross-linking is obtained through a synergistic interaction with a different polymer.

6. The method of claim 5, wherein said different polymer is a different polysaccharide.

7. The method of claim 1, wherein the polymer is based on a heteropolysaccharide of high molecular weight, obtained by fermentation of a carbohydrate by a microorganism of the genus Xanthomonas or Arthrobacter or fungus of the genus Sclerotium.

8. The method of claim 7, wherein the polysaccharide gel comprises at least one other polysaccharide of the group consisting of locust bean gum and natural gums.

9. The method of either claim 7 or 8, wherein a culture medium is first prepared and is seeded with the microorganism, the culture medium of the suspension of microorganism obtained by centrifuging or filtering the culture medium is then added to the polysaccharide solution, and the gel is formed by cooling.

10. The method of either claim 7 or 8, wherein a solution of polysaccharides is first prepared hot and brought to a temperature of 40°–45° C., the culture medium containing the microorganism or the suspension of the microorganism is added, and the mixture is then cooled to form a gel.

11. The method of claim 1, wherein the homogeneous moist preparation of the mycorrhizae microorganism is stored for at least several months.

12. The method of claim 1, wherein an inoculum is stored in the form of moist pellets, threads or fibers.

13. The method of claim 1, wherein the preparation is stored at ambient temperature.

* * * * *